United States Patent [19]

Cuny

[11] Patent Number: 5,370,109
[45] Date of Patent: Dec. 6, 1994

[54] DEFORMABLE ENDOSCOPIC SURGICAL RETRACTOR

[75] Inventor: Douglas J. Cuny, Bethel, Conn.

[73] Assignee: United States Surgical Corporation, Norwalk, Conn.

[21] Appl. No.: 21,157

[22] Filed: Feb. 19, 1993

[51] Int. Cl.$^5$ .......................... A61B 17/02; A61B 1/00
[52] U.S. Cl. .......................................... 128/20; 128/4; 606/198; 604/281
[58] Field of Search ................ 128/20, 17, 4 SM, 772, 128/4, 6–8; 606/198, 191; 604/281, 282, 165

[56] References Cited

U.S. PATENT DOCUMENTS

| | | |
|---|---|---|
| 3,620,212 | 11/1971 | Fannon, Jr. et al. |
| 3,890,977 | 6/1975 | Wilson . |
| 4,033,331 | 7/1977 | Guss .................. 604/281 X |
| 4,596,564 | 6/1986 | Spetzler et al. ............ 604/281 |
| 4,601,283 | 7/1986 | Chikama .................. 128/4 SM |
| 4,665,906 | 5/1987 | Jervis . |
| 4,676,249 | 6/1987 | Arenas et al. ............ 604/282 X |
| 4,773,431 | 9/1988 | Lodomirski ............ 604/281 X |
| 4,846,812 | 7/1989 | Walker et al. ............ 128/768 |
| 4,920,967 | 5/1990 | Cottonaro et al. ............ 128/772 X |
| 5,025,799 | 6/1991 | Wilson .................. 604/281 X |
| 5,037,178 | 8/1991 | Stoy et al. . |
| 5,078,684 | 1/1992 | Yasuda .................. 604/281 X |
| 5,106,369 | 4/1992 | Christmas . |
| 5,122,155 | 6/1992 | Eberbach . |
| 5,168,864 | 12/1992 | Shockey .................. 128/4 |

OTHER PUBLICATIONS

"Development of Polymeric Shape Memory Material", Shirai et al., Dec. 1988.
"Shape Memory Polymer", Mitsubishi Heavy Industries America, 1992.
"Processing Instructions for Mitsubishi Shape Memory Polymer", Manual No. 1, Rev. 2.2, Mitsubishi Heavy Industries, Ltd., Apr. 1992.
"Tinel® Shape-Memory Alloys", Raychem Corporation, May 1989.
"Shape Memory Metal", Raychem Corporation, Jul. 1984.
"Designing With The Shape Memory Effect", Duerig et al., MRS Int'l. Mtg. on Adv. Mats., vol. 9, 1989.

Primary Examiner—Richard J. Apley
Assistant Examiner—Donna L. Maraglio

[57] ABSTRACT

The invention described herein provides a surgical apparatus for use in endoscopic or laparoscopic procedures having a tubular body which includes a first substantially tractable section having a preformed configuration and a second substantially firm section defining a longitudinal axis, and a reciprocable rod member disposed within the tubular body and movable between a retracted position and a protracted position for progressively deforming the first section of the tubular body.

15 Claims, 4 Drawing Sheets

DEFORMABLE ENDOSCOPIC SURGICAL RETRACTOR

BACKGROUND OF THE INVENTION

1. Field of the Invention

This invention relates to surgical retractor apparatus, and more particularly, to apparatus for retracting organs or body tissue during endoscopic or laparoscopic surgical procedures.

2. Description of Related Art

In laparoscopic and endoscopic procedures, surgery is performed through a small incision made in the patient's body, generally to provide access for a trocar or cannula device. Once extended into the patient's body, the cannula device permits insertion of a variety of surgical instruments including scissors, graspers, and staplers.

Surgical retractors for use in endoscopic and laparoscopic surgical procedures are also known in the art. However, prior art endoscopic retractors are often inherently limited in their ability to effect retraction of large organs. This limitation results from the fact that the operative surface area of the retractor portions of many of these instruments is limited by the diameter of the trocar or cannula device through which the instrument must pass to be introduced to the operative site. In the past, this limitation has been overcome through the use of mechanical linkages having a plurality of moving parts which expand the surface area of the retractor portion once the instrument has been extended through the cannula device. However, instruments having linkage assemblies are often expensive to manufacture.

Therefore, it is an object of the subject invention to provide a surgical retractor for use in endoscopic or laparoscopic procedures having a variably configurable operative surface area.

It is another object of the subject invention to provide a surgical retractor for use in endoscopic and laparoscopic procedures which is inexpensive to manufacture.

It is another object of the subject invention to provide a surgical retractor for use in endoscopic or laparoscopic procedures which has a minimum number of external moving parts.

It is yet another object of the subject invention to provide a surgical retractor for use in endoscopic or laparoscopic procedures having a substantially atraumatic retractor portion.

These and other objects of the surgical apparatus of the subject invention will become more readily apparent from the following detailed description of the invention.

SUMMARY OF THE INVENTION

A novel surgical apparatus is provided for performing retraction tasks during endoscopic or laparoscopic procedures. The apparatus comprises a tubular member having a first substantially tractable section with a preformed configuration and a second substantially firm section defining a longitudinal axis. A reciprocal rod member is disposed within the tubular member and is movable in a longitudinal direction between a retracted position spaced from the first section and a protracted or extended position disposed at least partially within the first section. In operation, movement of the reciprocal rod member from the retracted position to the protracted position will cause the tractable section of the tubular member to deform from its preformed configuration.

The apparatus of the subject invention further comprises actuation means for remotely moving the reciprocal rod member between the retracted and protracted positions. Preferably, the actuation means includes an elongated axial control shaft extending through the tubular member and having an actuator disposed at the proximal end thereof for user manipulation, and having a coupling at the distal end thereof for mounting the reciprocal rod member thereto.

In a preferred embodiment of the subject invention, the first section of the tubular member is formed of a heat responsive thermoplastic material which is substantially tractable within a predetermined temperature range and which is not substantially tractable below the predetermined temperature range. When the thermoplastic material becomes substantially tractable at temperatures within the predetermined temperature range, and in the absence of an applied stress, the first section will assume a preformed configuration to effectuate retraction of organs or body tissue. After utilization, the first section may be deformed from its preformed configuration by applying a stress thereto. In the present invention, the stress is applied to the first section of the tubular member by progressively moving the reciprocable rod member from a retracted position spaced from the first section to a protracted position disposed within the first section of the tubular member.

Further features of the subject invention will become more readily apparent from the following detailed description of the invention taken in conjunction with the drawings.

BRIEF DESCRIPTION OF THE DRAWINGS

Preferred embodiments of the subject invention are described hereinbelow with respect to the drawings wherein.

DETAILED DESCRIPTION OF THE PREFERRED EMBODIMENTS

Figure 1:
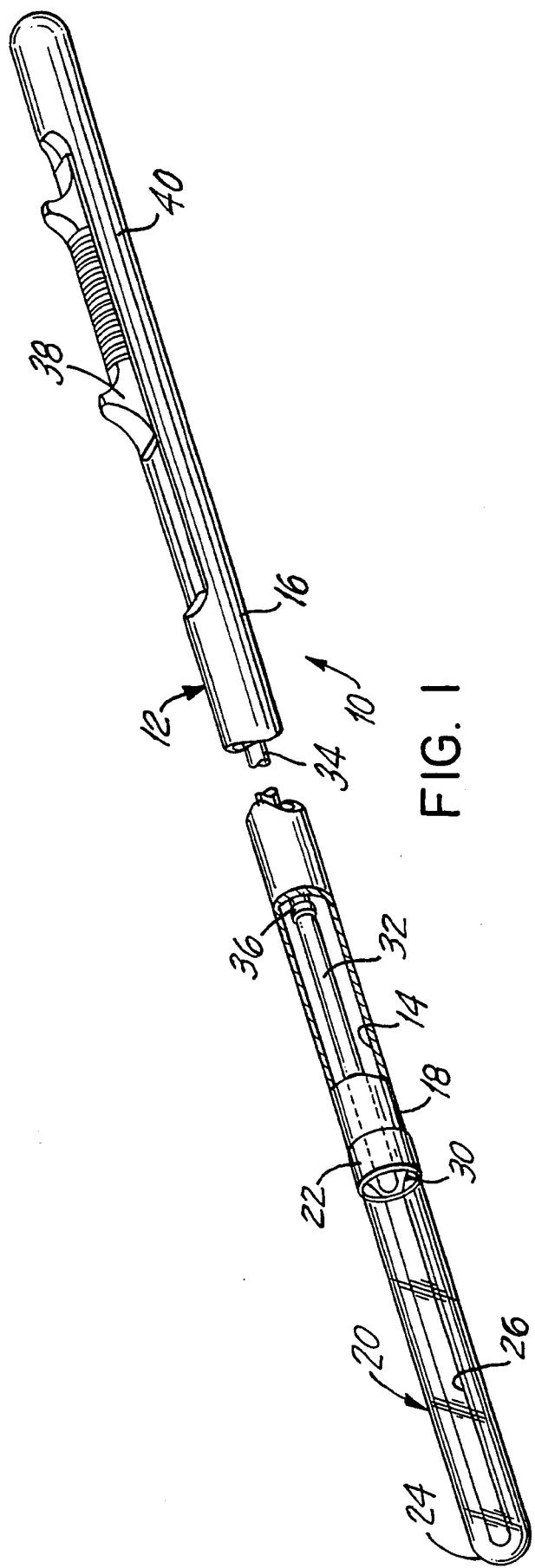
FIG. 1 is a perspective view in partial cross-section of a surgical apparatus in accordance with a preferred embodiment of the subject invention with the retractor portion thereof in an unstressed deformed position.

Because endoscopic procedures are more common than laparoscopic procedures, the present invention shall be discussed in terms of endoscopic procedures and apparatus. However, use herein of terms such as "endoscopic", "endoscopically", and "endoscopic portion", among others, should not be construed to limit the present invention to an apparatus for use only in conjunction with an endoscopic tube. To the contrary, it is believed that the present invention may find use in procedures wherein access is limited to a small incision including but not limited to laparoscopic procedures.

In the drawings and in the description which follows, the term "proximal", as is traditional, will refer to the end of the apparatus which is closest to the operator, while the term "distal" will refer to the end which is furthest from the operator.

Referring now in detail to the drawings, wherein like reference numerals identify similar elements, a surgical apparatus for performing retraction tasks during endoscopic or laparoscopic procedures in accordance with a preferred embodiment of the subject invention is illustrated in FIG. 1 and is designated generally by reference numeral 10. Surgical apparatus 10 comprises an elongated tubular body portion 12 defining an axial passageway 14 which extends from the proximal end 16 of body portion 12 to the distal end 18 thereof. Body portion 12 is preferably formed of a firm, lightweight, plastic material such as, for example, LEXAN brand material which is marketed by General Electric Corporation.

A substantially tractable retractor section 20 is mounted at the distal end 18 of body portion 12 by an annular mounting collar 22. Alternatively, retractor section 20 may be monolithically formed with body portion 12. Retractor section 20 has an atraumatic tip portion 24 at the distal end thereof and an axial cavity 26 extends partially therethrough from the proximal end 28 thereof. The cross-sectional diameters of retractor section 20 and tubular member 12 are substantially equal and are suitably dimensioned for endoscopic utilization. Retractor section 20 is preferably formed of a shape memory thermoplastic material which assumes a preformed configuration in the absence of an applied stress. Moreover, the material is a heat responsive thermoplastic material which will become substantially tractable within a predetermined temperature range. In particular, the material has a glass transition temperature in the range of about 20° C. to 40° C. It is within this temperature range that the internal body temperature of most warm blooded animals lie. The specific glass transition temperature of the material from which retractor section 20 is formed however, will depend upon the subject being operated on. For example, in veterinary procedures, the preferred glass transition temperature of the material may differ from that which is preferred in surgical procedures involving human subjects. Preferably, for surgical procedures involving human subjects the material from which retractor section 20 is formed is a shape memory polyurethane based polymer having a glass transition temperature of about 30° C. Therefore, at temperatures above about 30° C. (i.e. inside the patient's body) and in the absence of an applied stress, the polyurethane material from which retractor section 20 is formed will exhibit elastic or spring-like attributes and will assume its preformed configuration. Conversely, at temperatures below about 30° C. (i.e. outside the patient's body), retractor section 20 will remain rigid or glassy and will not be responsive to an applied stress.

The entry 30 to the axial cavity 26 formed in retractor section 20 is inwardly tapered to define a guideway for assisting the entry of a reciprocable straightener rod 32 into axial cavity 26 from an undeployed retracted position substantially within the axial passageway 14 of body portion 12. Reciprocal straightener rod 32 is preferably formed from a material which is sufficiently rigid to deform retractor section 20 from a preformed position. An example of a material which satisfies this requisite characteristic is stainless steel. The proximal end of reciprocal straightener rod 32 is mounted to a control shaft 34 at a connective end portion 36 thereof. Control shaft 34 extends longitudinally through axial passageway 14 and is configured for longitudinal translation with respect to body portion 12. A slide actuator 38 which is associated with handle portion 40 is interconnected to the proximal end of control shaft 34 for facilitating remote user actuation of apparatus 10.

In use, the apparatus may be introduced into the abdominal cavity of a patient through an incision or, alternatively, through a trocar or cannula device (not shown) which is inserted into a small incision in the patient's body. Because retractor section 20 remains substantially firm at room temperature, its insertion through the trocar or cannula device is smooth and unobstructed. However, once extended into the abdomen, the shape memory thermoplastic material from which retractor section 20 is formed, advantageously becomes tractable. As explained hereinabove, the change in rigidity of retractor section 20 is due to the relationship between the glass transition temperature of the material and the body temperature of the patient. Accordingly, once introduced to the operative site, the patient's body temperature, which is preferably above the glass transition temperature of the material, causes retractor section 20 to become flexible and conform to its preformed shape. At such a time, the surgeon may manipulate the instrument to effect retraction of large organs or body tissue.

Figure 2:
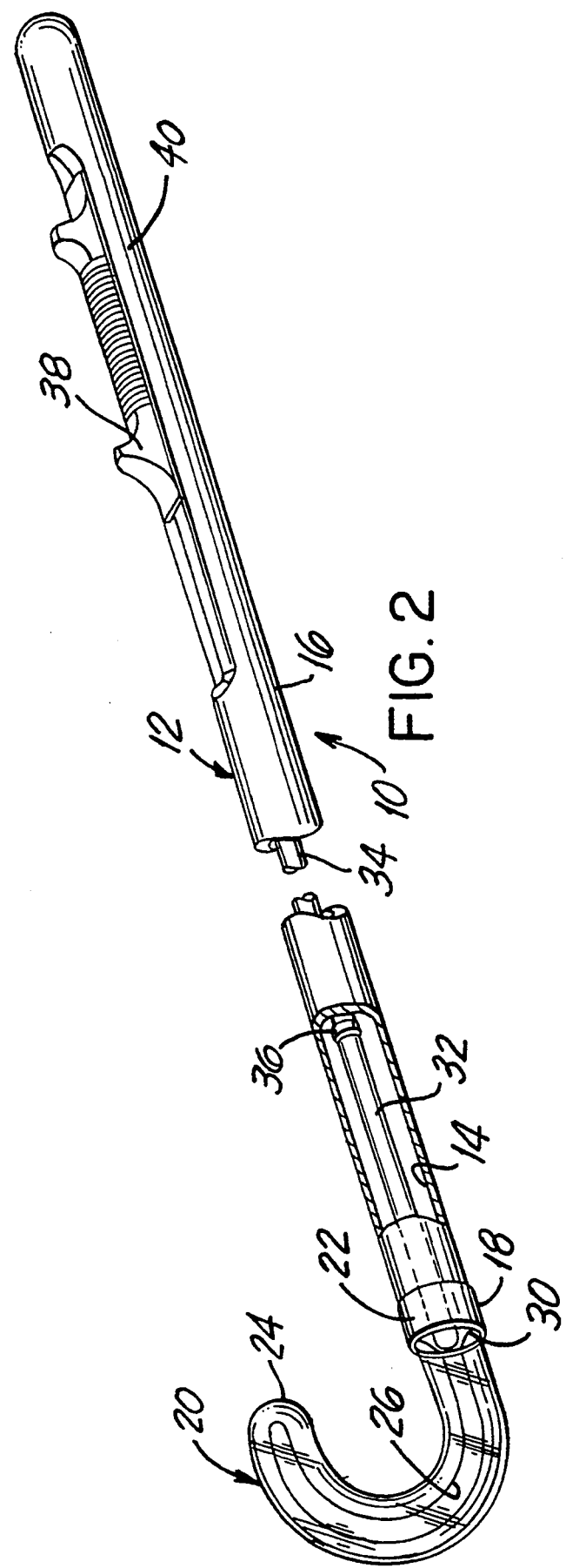
FIG. 2 is a perspective view in partial cross-section of the surgical apparatus of FIG. 1 with the retractor portion thereof in an unstressed preformed position.
Figure 3:
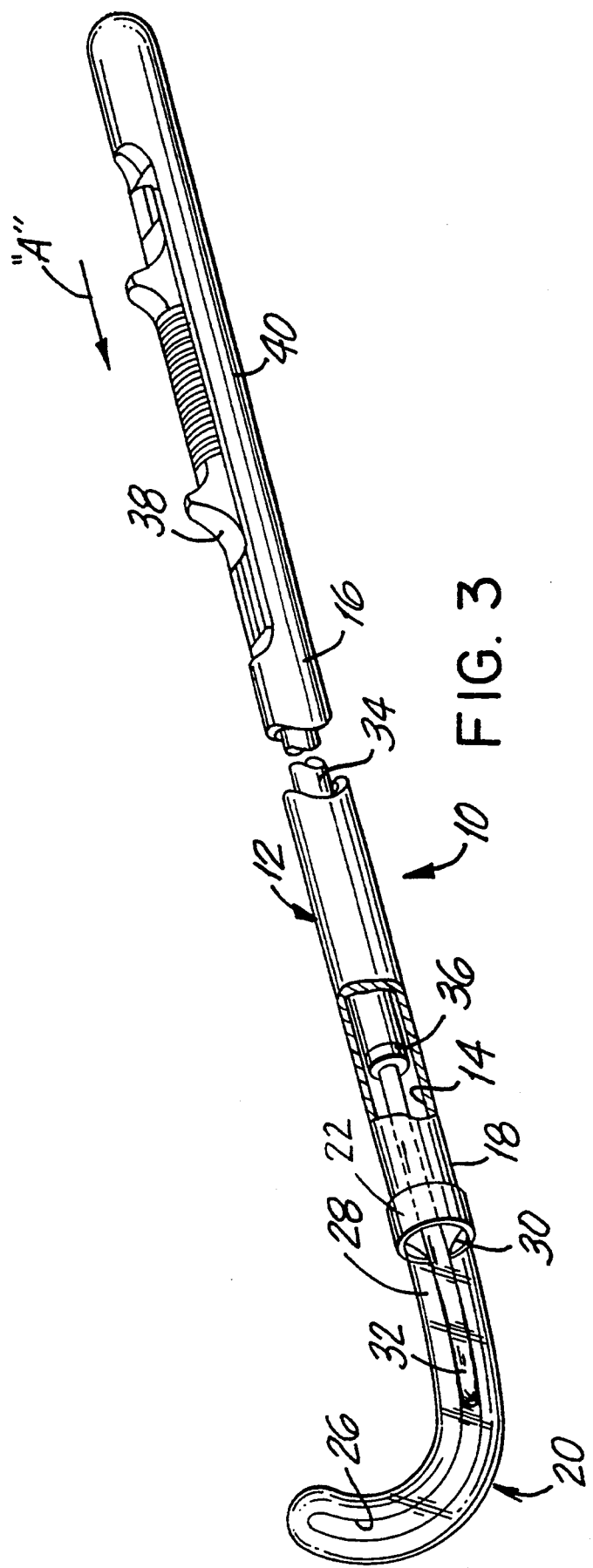
FIG. 3 is a perspective view in partial cross-section of the surgical apparatus of FIG. 1 with the retractor portion thereof in a partially deformed stressed position.
Figure 4:
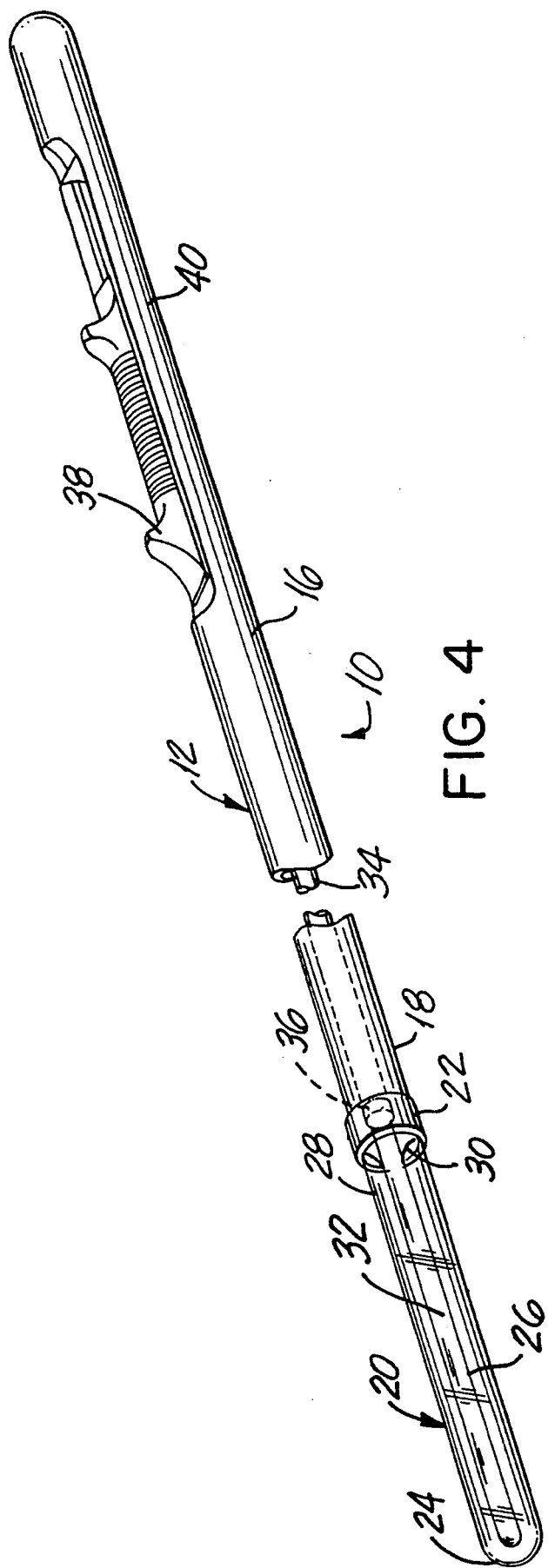
FIG. 4 is a perspective view of the surgical apparatus of FIG. 1 with the retractor portion thereof in a fully deformed stressed position.

At the conclusion of a retraction task, the operator, by exerting an axially applied force upon slide actuator 38 in the direction indicated by arrow "A" in FIG. 3, can urge control shaft 34 in a distal direction, driving the reciprocal straightener rod 32 forward. Initially, the distal end of reciprocal rod 32 is guided into the axial cavity 26 of retractor portion 20 by the tapered entry 30 defined therein. As the reciprocable straightener rod 32 extends into axial cavity 26, retractor section 20 progressively deforms from its preformed configuration, moving from the unstressed position of FIG. 2 to the stressed position of FIG. 4. Once straightener rod 32 has been fully protracted or extended into cavity 26, retractor portion 20 will be in substantial alignment with the longitudinal axis defined by body portion 12. At such a time, surgical apparatus 10 may be removed from the operative site through a trocar or cannula device without obstruction.

Preferably, as illustrated in FIG. 2, the preformed shape of retractor section 20 is substantially U-shaped in configuration such that, when fully deployed, the distal end portion of the instrument 10 defines a generally J-shaped atraumatic retractor mechanism suitable for manipulating large organs or body tissue during endoscopic or laparoscopic surgical procedures. Other retractor configurations are envisioned, including, for example, a retractor defining a substantially continuous loop, or one which extends substantially angularly from the longitudinal axis of the instrument.

Although the surgical apparatus of the subject invention has been described with respect to a preferred embodiment, it is apparent that changes or modifications made be made thereto without departing from the spirit or scope of the invention as defined by the appended claims.

What is claimed is:

1. A surgical apparatus comprising:
   a) a tubular member including a first substantially tractable section defining an imperforate outer wall and having a stressed configuration and a preformed unstressed configuration, said tractable section formed of a heat responsive material which when heated within a predetermined temperature range, in the absence of an applied stress, assumes said unstressed configuration, and a second substantially firm section defining a longitudinal axis; and b) a reciprocable rod member disposed within said tubular member and movable in a longitudinal direction between a retracted position spaced from said first section and a protracted position disposed at least partially within said first section, whereby progressive movement of said rod member into said first section will impart a stress thereto so as to progressively deform said first section into said stressed configuration.

2. A surgical apparatus as recited in claim 1, further comprising means for remotely moving said reciprocable rod member in a longitudinal direction with respect to said tubular member.

3. A surgical apparatus as recited in claim 1, wherein said first section of said tubular member is formed of a heat responsive thermoplastic material having a glass transition temperature of between about 20° C. and 40° C.

4. A surgical apparatus as recited in claim 3, wherein said heat responsive thermoplastic material is a polyurethane based polymer having a glass transition temperature of about 30° C.

5. A surgical apparatus as recited in claim 1, wherein said first section of said tubular member has a substantially arcuate posture in said preformed unstressed configuration.

6. A surgical apparatus as recited in claim 1, wherein said first section of said tubular member is in substantial alignment with said longitudinal axis of said second section in said stressed configuration.

7. A surgical apparatus comprising:
a) a tubular member having a first section defining an imperforate outer wall and formed of a heat responsive thermoplastic material which is substantially tractable within a predetermined temperature range and which is not substantially tractable below said predetermined temperature range, said first section assuming, in the absence of an applied stress, a preformed configuration when said thermoplastic material is at a temperature within said predetermined temperature range, and a second substantially firm section defining a longitudinal axis; and b) a reciprocable rod member disposed within said tubular member and movable in a longitudinal direction between a retracted position spaced from said first section and a protracted position disposed at least partially within said first section, whereby at temperatures substantially within said predetermined temperature range progressive movement of said rod member into said first section will impart a stress thereto so as to progressively deform said first section into a stressed configuration.

8. A surgical apparatus as recited in claim 7, further comprising actuation means for remotely moving said reciprocable rod member relative to said tubular member.

9. A surgical apparatus as recited in claim 8, wherein said actuation means comprises an axial control shaft coupled to said reciprocable rod member and movable in a longitudinal direction with respect to said tubular member.

10. A surgical apparatus as recited in claim 7, wherein said heat responsive thermoplastic material is a polyurethane based polymer having a glass transition temperature of between about 20° C. and 40° C.

11. A surgical apparatus as recited in claim 7, wherein said first section of said tubular member has a substantially arcuate posture in said preformed configuration.

12. A surgical apparatus as recited in claim 7, wherein said first section of said tubular member is in substantial alignment with said longitudinal axis of said second section in said stressed configuration.

13. A surgical apparatus as recited in claim 7, wherein said first section of said tubular member has a diameter which is substantially equal to a diameter of said second section of said tubular member.

14. A surgical apparatus as recited in claim 7, wherein said tubular member is dimensioned for endoscopic utilization.

15. A surgical apparatus comprising:
a) a tubular member including a first substantially tractable section formed of a heat responsive material which assumes a preformed configuration within a predetermined temperature range, said first section having an imperforate outer wall, and a second substantially firm section having a longitudinal axis; and b) a reciprocable rod member disposed within said tubular member and remotely movable in a longitudinal direction between a retracted position spaced from said first section and a protracted position disposed at least partially within said first section, and wherein said first section is disposed in said preformed configuration when said rod member is in said retracted position and said first section is heated within said predetermined temperature range, and said first section deforms from said preformed configuration when said rod member is moved toward said protracted position.

* * * * *